United States Patent
Kirsch et al.

(10) Patent No.: US 9,956,068 B2
(45) Date of Patent: May 1, 2018

(54) PACKAGE FOR A SURGICAL REPAIR KIT

(71) Applicant: Covidien LP, Mansfield, MA (US)

(72) Inventors: David Kirsch, Madison, CT (US); Moses Chellappa, Rochester Hills, MI (US)

(73) Assignee: Covidien LP, Mansfield, MA (US)

( * ) Notice: Subject to any disclaimer, the term of this patent is extended or adjusted under 35 U.S.C. 154(b) by 300 days.

(21) Appl. No.: 14/023,496

(22) Filed: Sep. 11, 2013

(65) Prior Publication Data
US 2014/0090999 A1 Apr. 3, 2014

Related U.S. Application Data

(60) Provisional application No. 61/706,851, filed on Sep. 28, 2012.

(51) Int. Cl.
| | | |
|---|---|---|
| A61B 19/02 | (2006.01) | |
| A61F 2/00 | (2006.01) | |
| A61B 17/00 | (2006.01) | |
| A61B 50/30 | (2016.01) | |
| A61B 50/00 | (2016.01) | |

(52) U.S. Cl.
CPC ........ *A61F 2/0095* (2013.01); *A61B 17/0057* (2013.01); *A61B 50/30* (2016.02); *A61F 2/0063* (2013.01); *A61B 2017/00641* (2013.01); *A61B 2050/0056* (2016.02); *A61B 2050/0067* (2016.02); *A61B 2050/3008* (2016.02)

(58) Field of Classification Search
CPC ................ A61B 17/0057; A61B 50/30; A61B 2050/3008; A61F 2002/0068
USPC ....... 206/440, 438, 5.1, 370, 441, 63.3, 828, 206/363, 499; 606/151; 333/440, 438
See application file for complete search history.

(56) References Cited

U.S. PATENT DOCUMENTS

| | | | |
|---|---|---|---|
| 3,987,895 A | * | 10/1976 | Jamshidi ................ B65D 51/26 206/223 |
| 4,279,344 A | | 7/1981 | Holloway, Jr. |
| 4,596,329 A | * | 6/1986 | Eldridge, Jr. ................ 206/232 |
| 5,116,357 A | | 5/1992 | Eberbach |
| 5,249,682 A | | 10/1993 | Transue |
| 5,494,162 A | | 2/1996 | Treace et al. |
| 5,669,501 A | | 9/1997 | Hissong et al. |
| 5,690,226 A | | 11/1997 | N'Guyen |
| 5,699,909 A | | 12/1997 | Foster |
| 5,972,008 A | | 10/1999 | Kalinski et al. |
| 6,000,548 A | | 12/1999 | Tsals |
| 6,059,111 A | | 5/2000 | Davila et al. |
| 6,234,310 B1 | | 5/2001 | Goldhaber |
| 6,588,586 B2 | | 7/2003 | Abasolo et al. |
| 6,854,599 B2 | | 2/2005 | Ferrara, Jr. et al. |
| 6,969,197 B2 | | 11/2005 | Sedley |

(Continued)

FOREIGN PATENT DOCUMENTS

WO 2006100372 A1 9/2006

OTHER PUBLICATIONS

European Search Report, Application No. EP 13 18 6536 dated Jan. 15, 2014.

*Primary Examiner* — J. Gregory Pickett
*Assistant Examiner* — Allan Stevens

(57) ABSTRACT

The present disclosure relates to a package for a surgical repair kit, the package including at least a first area configured and dimensioned to receive a surgical mesh and a second area configured and dimensioned to receive an implantable plug.

25 Claims, 5 Drawing Sheets

(56) References Cited

U.S. PATENT DOCUMENTS

| | | |
|---|---|---|
| 6,976,584 B2 | 12/2005 | Maiola et al. |
| 6,991,096 B2 | 1/2006 | Gottlieb et al. |
| 6,991,597 B2 | 1/2006 | Gellman et al. |
| 7,093,595 B2 * | 8/2006 | Nesbitt .............. A61M 15/0045 128/203.15 |
| 7,108,711 B2 | 9/2006 | Vogel et al. |
| 7,243,791 B2 | 7/2007 | Detruit et al. |
| 7,293,646 B2 | 11/2007 | Masuda et al. |
| 7,308,985 B2 | 12/2007 | Riley |
| 7,320,404 B2 | 1/2008 | Landis |
| 7,398,877 B1 * | 7/2008 | Nelson ................. A45C 11/005 134/901 |
| 7,481,314 B2 | 1/2009 | Komarnycky |
| 7,648,030 B2 | 1/2010 | Landis |
| 7,694,814 B1 | 4/2010 | Cristobal et al. |
| 7,766,164 B2 | 8/2010 | Hurst |
| 7,850,006 B2 | 12/2010 | Uchiyama |
| 7,870,959 B2 | 1/2011 | Kuo et al. |
| 7,967,139 B2 | 6/2011 | Brinker |
| 8,002,113 B1 | 8/2011 | Cummings |
| 8,006,839 B2 | 8/2011 | Hafner |
| 2002/0099258 A1 | 7/2002 | Staskin et al. |
| 2002/0117408 A1 | 8/2002 | Solosko et al. |
| 2003/0100954 A1 * | 5/2003 | Schuldt-Hempe .... A61F 2/0063 623/23.72 |
| 2004/0000499 A1 | 1/2004 | Maiola et al. |
| 2004/0039453 A1 | 2/2004 | Anderson et al. |
| 2004/0068159 A1 | 4/2004 | Neisz et al. |
| 2004/0154946 A1 | 8/2004 | Solovay et al. |
| 2004/0188302 A1 | 9/2004 | Rogers, Jr. |
| 2005/0077197 A1 | 4/2005 | Detruit et al. |
| 2005/0087456 A1 | 4/2005 | Oka et al. |
| 2005/0098460 A1 | 5/2005 | Smith et al. |
| 2005/0126948 A1 | 6/2005 | Maiola et al. |
| 2005/0226795 A1 | 10/2005 | Drummond et al. |
| 2005/0269231 A1 | 12/2005 | White et al. |
| 2006/0282045 A1 | 12/2006 | Wilkinson et al. |
| 2007/0084742 A1 * | 4/2007 | Miller ................ A61B 17/3472 206/438 |
| 2007/0123915 A1 * | 5/2007 | Kammerer ............ A61F 2/0045 606/151 |
| 2008/0073233 A1 | 3/2008 | Landis |
| 2009/0198119 A1 | 8/2009 | Niederberger et al. |
| 2010/0036736 A1 | 2/2010 | Knowlton et al. |
| 2010/0078347 A1 | 4/2010 | Brinker |
| 2010/0133133 A1 | 6/2010 | Hamas |
| 2010/0155282 A1 | 6/2010 | Govil et al. |
| 2010/0200778 A1 | 8/2010 | Drobnik et al. |
| 2010/0219092 A1 | 9/2010 | Salahieh et al. |
| 2011/0036736 A1 | 2/2011 | Knowlton et al. |
| 2011/0154889 A1 | 6/2011 | Stafford et al. |

* cited by examiner

PACKAGE FOR A SURGICAL REPAIR KIT

CROSS-REFERENCE TO RELATED APPLICATIONS

This application claims the benefit of and priority to U.S. Provisional Patent Application No. 61/706,851, filed Sep. 28, 2012, the entire disclosure of which is incorporated by reference herein.

BACKGROUND

Technical Field

The present disclosure relates generally to packaging for a surgical repair kit, and more particularly, packaging for a surgical repair kit which includes at least one surgical mesh and at least one surgical plug.

Background of the Related Art

Surgical meshes are typically employed to repair or obturate an opening in tissue or a wound, such as a hernia or fistula. The surgical mesh may be positioned across the opening in a generally planar configuration to support the tissue and/or wound. In some instances, the opening in the tissue and/or wound may have a depth that spans multiple layers of tissue, such as a ventral hernia or colostomy. In such instances, the surgical mesh may be combined with a surgical plug to further support the depth of the opening.

Conventional techniques for transporting and storing such devices may not be entirely satisfactory. These techniques may lead to damage or alteration of the shape of the surgical mesh and/or the surgical plug. The surgical plug, typically having a three-dimensional configuration, i.e., a cylindrical or conical configuration, may be intended to be inserted into a hernial canal of corresponding size and shape. The shape of the device facilitates the insertion and placement of the device for treatment of hernias. If the device is crushed during shipping, it may be difficult for the surgeon to use the device and properly place it in the patient. Therefore, the maintenance of the shape of the surgical mesh and/or the surgical plug may be important.

However, since surgical mesh and/or surgical plugs may often by configured to be sufficiently flexible to be rolled, folded, and/or reconfigured prior to implantation, it may be difficult to prevent alteration of such implants during manufacturing, sterilizing, shipping and/or storing. It would be beneficial to provide packages suitable for storing and/or receiving a surgical mesh and a surgical plug which maintains the shape of the surgical mesh and the surgical plug separately.

SUMMARY

The present disclosure describes packages for a surgical repair kit which includes a first area configured and dimensioned to receive at least one surgical mesh and a second area configured and dimensioned to receive at least one surgical plug, wherein the mesh and the plug are maintained separate from each other.

In embodiments, the first area includes at least one recess for storing a portion of the mesh and/or another implantable device. In embodiments, the second area includes at least one protrusion extending from the base of the second area for storing the surgical plug. In embodiments, the protrusion generally follows the contour of the implantable surgical plug.

In embodiments, the packages described herein may further include an intermediate wall which separates the first and second areas of the package. In some embodiments, the intermediate wall also includes at least one protrusion. In some embodiments, the at least one protrusion of the intermediate wall may be vertically aligned with the protrusion of the second area.

The present disclosure further describes packages for a surgical repair kit which includes a first and second compartment which are separately sealable. The first compartment is configured and dimensioned to receive at least one surgical mesh. The second compartment is configured and dimensioned to receive at least one surgical plug. In embodiments, the first compartment includes at least one recess for storing a portion of the mesh and/or another implantable device. In embodiments, the second compartment includes at least one protrusion extending from the base of the second compartment for storing the surgical plug. In embodiments, the protrusion generally follows the contour of the implantable surgical plug.

In embodiments, the packages described herein may further include an intermediate wall which separates the first and second sealable compartments of the package. In some embodiments, the intermediate wall also includes at least one protrusion. In some embodiments, the at least one protrusion of the intermediate wall may be vertically aligned with the protrusion of the second compartment.

BRIEF DESCRIPTION OF THE DRAWINGS

The foregoing objects and advantages of the present disclosure will become more apparent from the reading of the following description in connection with the accompanying drawings, in which.

DETAILED DESCRIPTION

Figure 1A:
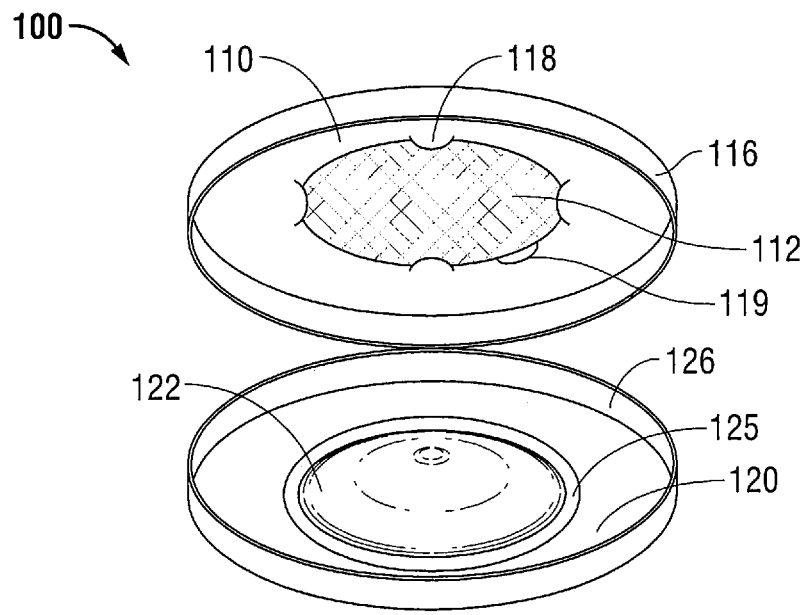
FIGS. 1A and 1B include a perspective view and a side view, respectively, of a package according to at least one embodiment described herein.

Reference will now be made to the drawings wherein like structures are provided with like reference designations. It will be understood that the drawings included herewith only provide diagrammatic representations of the packages of the present disclosure and that packages falling within the scope of the present disclosure may include structures different than those shown in the drawings.

Figure 1B:
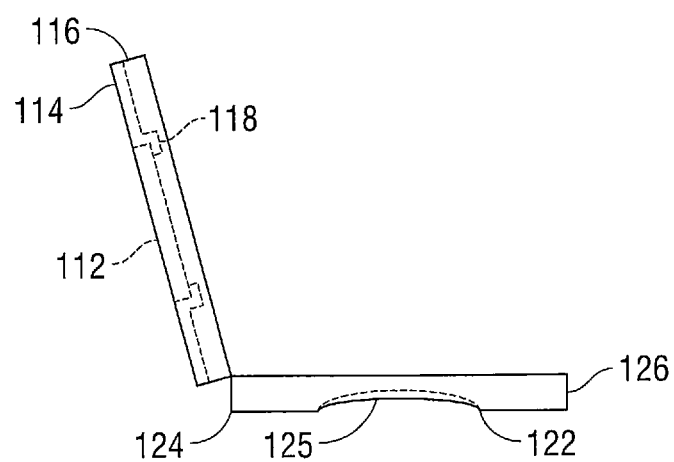

Turning now to FIGS. 1A and 1B, a package for a hernia repair kit in an open position is shown. Package 100 includes first area 110 configured to receive at least one surgical mesh 112 and second area 120 configured to receive at least one surgical plug 122. Package 100 is shown as circular; however the package may be of any shape suitable for receiving a surgical mesh and a surgical plug. In embodiments, package 100 includes top 114, base 124, at least one top side wall 116 which extends from top 114 towards base 124, and at least one base side wall 126 which extends from base 124 towards top 114. Top 114 and base 214 are pivotably attached to open and/or close package 100. For example, the top and the base may attach via a hinge. Top side wall 116 and base side wall 126 define an outer perimeter of package 100 and may be designed to matingly engage to close package 100.

In FIGS. 1A and 1B, top 114 is shown as generally flat and includes a generally flat mesh implant. Top 114 further includes at least one holding member 118 which may be used to press mesh 112 against the inside of top 114 thereby locking mesh 112 against top under pressure. It is envisioned that the at least one holding member may not only be used to store the mesh in a flat configuration, but may also be used to store the mesh in a three-dimensional configuration, such as when a mesh is rolled and/or folded (not shown).

In addition, top 114 may further include at least one access guide 119 which may provide access to beneath mesh 112 for removal of mesh 112 from first area 110 of package 100.

In some embodiments, as further shown in FIGS. 1A and 1B, plug 122 may be positioned on at least one protrusion 125 formed in base 124. In some embodiments, protrusion 125 may generally follow the contour of plug 122. In some embodiments, protrusion 125 may be at least slightly larger than plug 122 to raise plug 122 off base 124. It is envisioned that a plug which is raised off the base may be easier to remove from the package, than a plug that contacts the base.

Figure 2A:
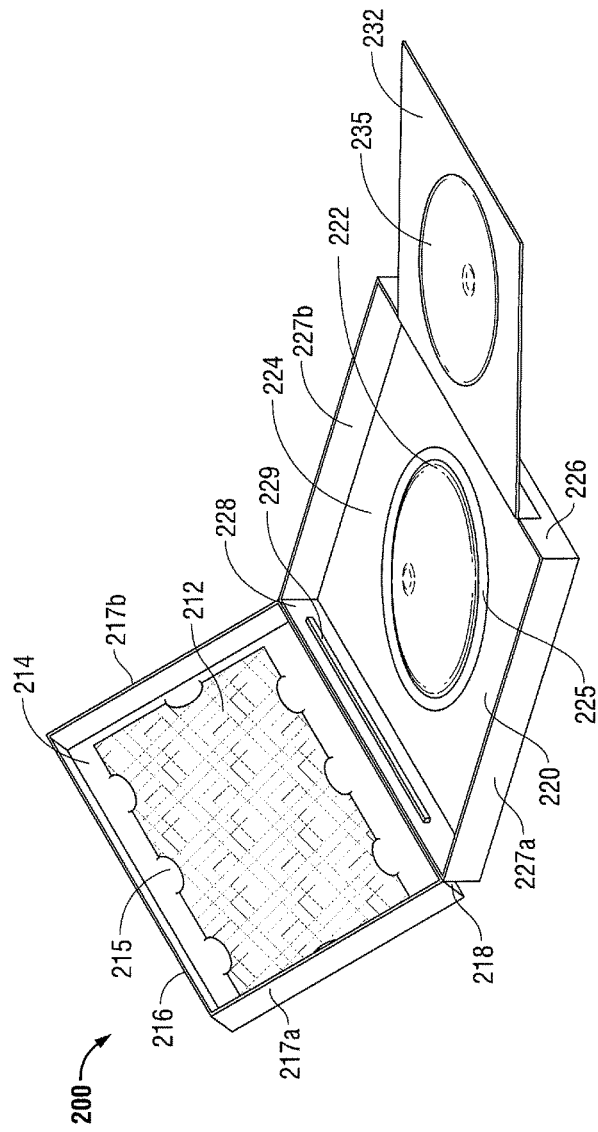
FIGS. 2A, 2B and 2C include a perspective view and two side views, respectively, of a package according to at least one embodiment described herein.
Figure 2B:
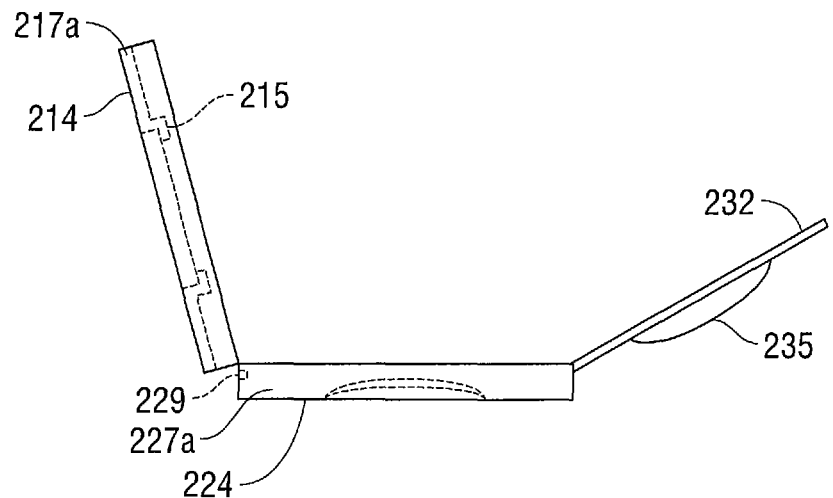

Turning now to FIGS. 2A and 2B, package 200 is shown in an open position and includes top 214, base 224 and intermediate wall 232. Top 214 includes top front wall 216, top side walls 217a, 217b and top rear wall 218. Base 224 includes base front wall 226, base side walls 227a, 227b and base rear wall 228. Top 214 and base 224 are pivotably attached via top rear wall 218 and base rear wall 228. Intermediate wall 232 is pivotably attached to base front wall 226 and is designed to fold towards base rear wall 228 to separate plug 222 from mesh 212 within package 200.

Top 214 includes a plurality of holding members 215 and at least one recess 219. In embodiments, recess 219 may be suitable in area to store the mesh in a flat and/or three-dimensional configuration. In some embodiments, recess 219 may be suitable to receive at least one surgical device tool, and/or fastener. For example, it is envisioned that the recess may store surgical fasteners such as sutures, staples, sealants, adhesives, glues, tacks, screws, pins, needles, clips, and the like. In some embodiments, it is envisioned that the recess may receive both the mesh and an additional surgical tool.

Base 224 includes at least one base protrusion 225 added to base 224. Base protrusion 225 is shown as centrally located on base 224. In embodiments, the base protrusion is a generally arcuate protrusion. In embodiments, the base protrusion is a generally cylindrical protrusion.

Intermediate wall 232 includes intermediate protrusion 235. In the closed position, intermediate protrusion 235 may be vertically aligned with base protrusion 225 to separate plug 222 from mesh 212. Base rear wall 228 may also include at least one tab 229 to prevent intermediate wall 232 from being lowered onto plug 222. In embodiments, tab 229 may extend along the entire length of base rear wall 228. In embodiments, tab 229 may extend only partially along the length of base rear wall 228. In still other embodiments, tab 229 may wrap around second compartment 220 along any portion of base side walls 227a, 227b and base front wall 226.

Figure 2C:
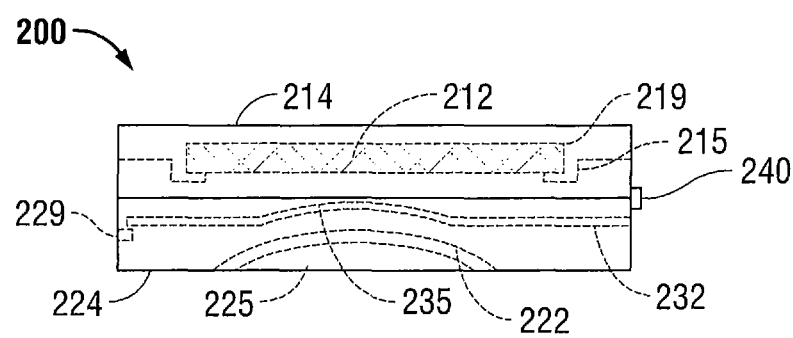

As depicted in FIG. 2C, package 200 may be generally rectangular and top 214, base 224, and intermediate wall 232, may be folded to close package 200. At least one latch 240 maintains package 200 in the closed position.

Figure 3A:
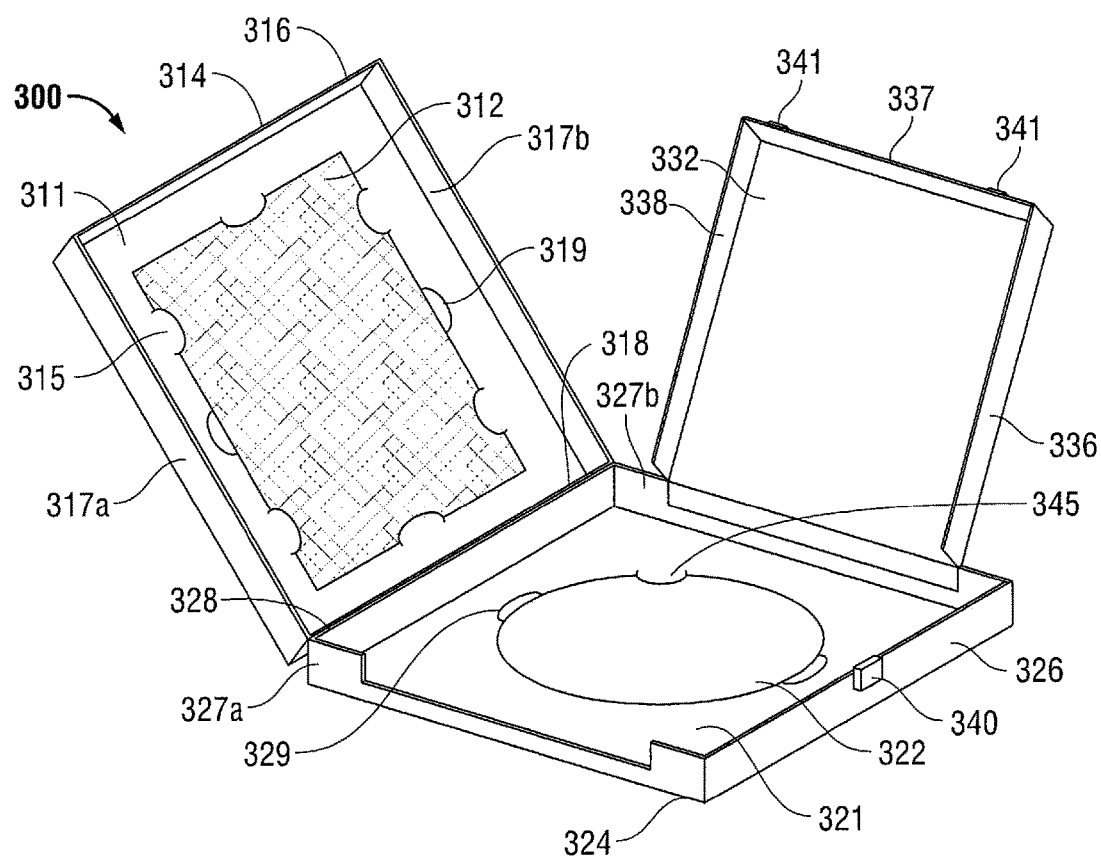
FIGS. 3A, 3B and 3C include two perspective views and a side view of a package according to at least one embodiment described herein.
Figure 3B:
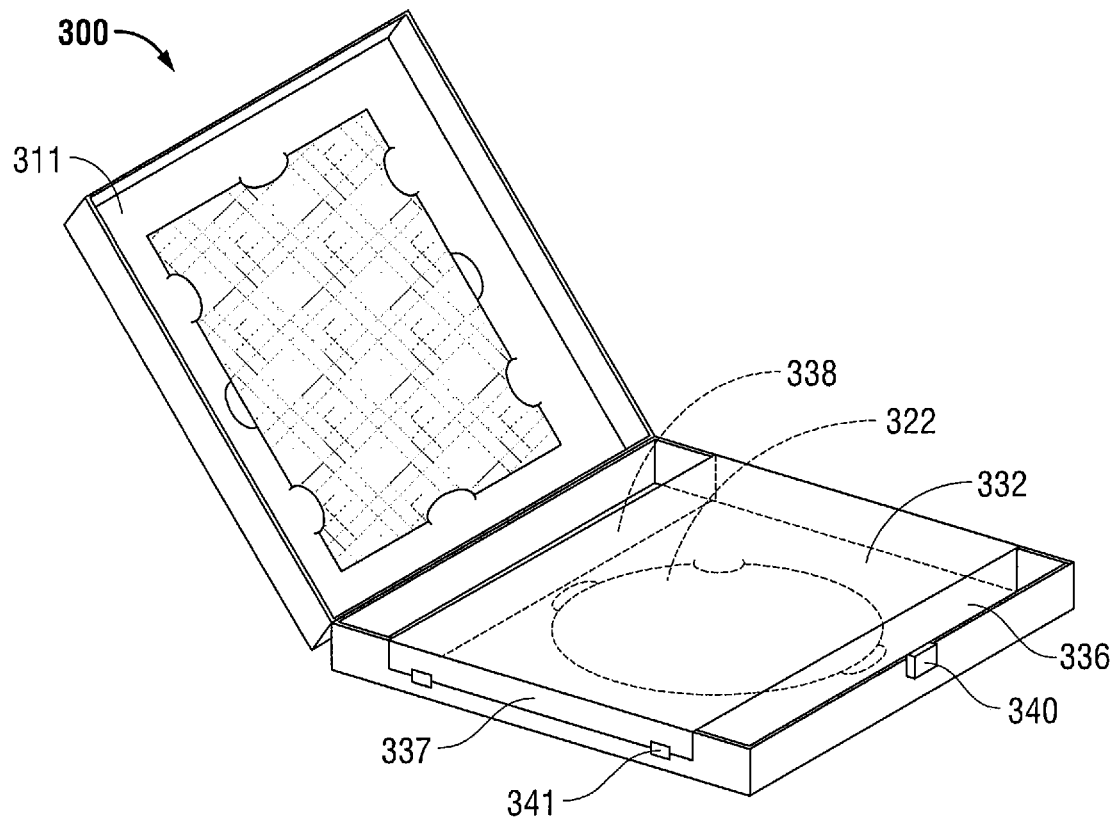

In FIGS. 3A and 3B, package 300 includes first sealable compartment 311 configured to receive mesh 312 and second sealable compartment 321 configured to receive plug 322. First sealable compartment 311 and second sealable compartment 321 include at least one holding members 315, 345 and access guides 319, 329. By sealable, the compartments and/or areas described herein may be hermetically sealed to maintain a sterile environment within the compartment and/or area in a closed position.

Package 300 is shown in an open position and includes top 314, base 324 and middle wall 332. Top 314 includes top front wall 316, top side walls 317a, 317b and top rear wall 318. Base 324 includes base front wall 326, base side walls 327a, 327b and base rear wall 328. Top 314 and base 324 are pivotably attached via top rear wall 318 and base rear wall 328. Intermediate wall 332 is pivotably attached to base side wall 327b and is designed to fold towards base side wall 327a to separate plug 322 from mesh 312 within package 300 in a closed position (see FIG. 3C).

Intermediate wall 332 includes intermediate front wall 336, intermediate rear wall 338 and at least one intermediate side wall 337. As shown in FIG. 3B, first compartment 311 may be in an open position while second compartment 321 is in a closed position. As illustrated in FIG. 3B, intermediate wall 332 may be folded to enclose plug 322 in second compartment 321 by intermediate front wall 336, intermediate rear wall 338 and at least one intermediate side wall 337. Package 300 is designed to allow access into each sealable compartment independently while maintaining the sterility of the other compartment(s).

Figure 3C:
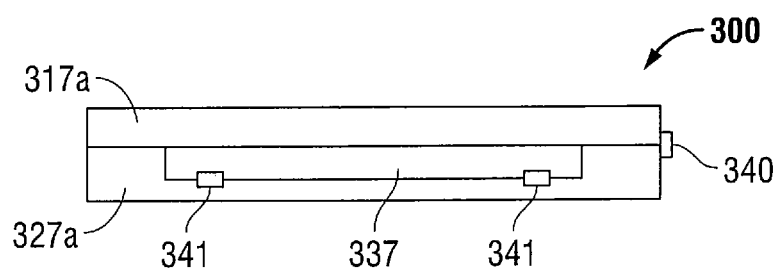

As depicted in FIG. 3C, package 300 may be generally rectangular and top 314, base 324, and intermediate wall 332, may be folded to close package 300. Second latch 341 may be positioned on the outside of intermediate side wall 337 to maintain second compartment 321 in a closed and sealed configuration. First latch 340 maintains first compartment 311 and/or package 300 in a closed position.

In embodiments, the packages described herein include at least one compartment. In embodiments, the packages described herein include two or more compartments. Each compartment described herein may be sealable to maintain the surgical mesh and/or surgical plug under sterile conditions and suitable for implantation.

In embodiments, the packages described herein may be opened one compartment at a time wherein the non-opened compartment may remain sealed and the sterility of the compartment is not compromised.

The packages for surgical repair kits described herein may be used for any suitable surgery which includes a mesh and a surgical plug. Some non-limiting examples include hernia repair kits, prolapse repair kits, and colostomy repair kits.

The packages described herein may be made from any suitable material which can be sterilized. Such materials include plastic, foils, combinations thereof and laminates thereof. In embodiments, the packages may be formed using any suitable molding process.

The packages described herein may be monolithic and/or made from multiple separate pieces. The packages may be manufactured using any conventional fabrication materials and techniques. The packages protect the mesh and the plug during sterilization, shipping and handling. The packages maintain the mesh and the plug in a position useable for its intended purposes in a hernia repair operation.

In addition, some of the packages described herein may be hermetically sealed and thus may not need to be stored in an additional outer package or envelope. In some embodiments, the packages described herein may not be hermetically sealed and may be further placed into a conventional plastic outer envelope or foil pouch, i.e., Tyvek peelable pouch, which is then sealed to maintain sterility of the package, plug and mesh. The sealed envelope or pouch may then be sterilized using any conventional sterilization process and further packaged for shipping.

What is claimed is:

1. A package for a surgical repair kit comprising:
   at least one surgical mesh and at least one surgical plug,
   a first area configured and dimensioned to receive the at least one surgical mesh, the first area including a top and at least one top side wall,
   a second area configured and dimensioned to receive the at least one surgical plug, the second area pivotably attached to the first area and including a base, a base protrusion, and at least one base side wall, and,
   an intermediate wall positioned between the first area and the second area, the intermediate wall including an intermediate protrusion, wherein the mesh and the plug are maintained separate from each other within the package, and wherein the base protrusion and the intermediate protrusion extend in a direction toward the top of the first area.

2. The package according to claim 1 wherein the first area configured and dimensioned to receive at least one surgical mesh is flat.

3. The package according to claim 1 wherein the first area configured and dimensioned to receive at least one surgical mesh further comprises a recess.

4. The package according to claim 1 wherein the first area configured and dimensioned to receive at least one surgical mesh further comprises at least one holding member.

5. The package according to claim 1 wherein the intermediate protrusion of the intermediate wall is vertically aligned with the base protrusion of the second area.

6. The package according to claim 1 further comprising at least one finger guide.

7. The package according to claim 1, wherein the at least one surgical mesh and at least one surgical plug are sterile.

8. A package for a surgical repair kit comprising:
   at least one surgical mesh and at least one surgical plug,
   a first compartment configured and dimensioned to receive the at least one surgical mesh, the first compartment including a top and at least one top wall,
   a second compartment configured and dimensioned to receive the at least one surgical plug, the second compartment pivotably attached to the first compartment and including a base and at least one base wall, the base comprising a base protrusion following a contour of the surgical plug, and
   an intermediate wall positioned between the first compartment and the second compartment, the intermediate wall including an intermediate protrusion, wherein the base protrusion and the intermediate protrusion extend in a direction toward the top of the first compartment.

9. The package according to claim 8, wherein at least one of the base protrusion and intermediate protrusion comprises an arcuate design.

10. The package according to claim 8, wherein the first compartment and the second compartment are connected via hinge.

11. The package according to claim 8, wherein the intermediate wall and the second compartment are connected via a hinge.

12. The package according to claim 8, wherein the intermediate protrusion of the intermediate wall is vertically aligned with the base protrusion of the base of the second compartment.

13. The package according to claim 8, wherein the first compartment comprises a flat area to receive the at least one surgical mesh.

14. The package according to claim 8, wherein the first compartment further comprises a recess.

15. The package according to claim 8, wherein the first compartment further comprises at least one holding member for securing the at least one surgical mesh in the first compartment.

16. The package according to claim 8, wherein the first compartment and the second compartment open separately.

17. The package according to claim 8, wherein the first compartment is sealable.

18. The package according to claim 8, wherein the second compartment is sealable.

19. The package according to claim 8, further comprising a locking member on an exterior portion of the package.

20. The package according to claim 8, further comprising at least one finger guide for assisting with the removal of at least one of the at least one surgical mesh and the at least one implantable plug.

21. The package according to claim 8, further comprising a tab extending along a length of a wall of the second compartment to prevent the intermediate wall from being lowered onto the surgical plug.

22. The package according to claim 8 wherein the at least one top wall includes a top front wall, top rear wall, and at least one top side wall and the at least one base wall includes a base front wall, a base rear wall, and at least one base side wall.

23. The package of claim 22, wherein the first compartment and the second compartment are pivotably attached via the top rear wall and the base rear wall and the intermediate wall is pivotably attached to base front wall and designed to fold towards base rear wall.

24. The package according to claim 8, wherein the at least one surgical mesh and the at least one surgical plug are sterile.

25. A package for storing a surgical repair kit, the package comprising:
   a surgical repair kit including at least one sterile surgical mesh and at least one sterile surgical plug,
   a first area configured and dimensioned to receive the at least one sterile surgical mesh, wherein the first area is flat and includes a top and at least one top side wall,
   a second area configured and dimensioned to receive the at least one sterile surgical plug, the second area pivotably attached to the first area and including a base and at least one base side wall, wherein the base of the second area includes a base protrusion, and,
   an intermediate wall positioned between the first area and the second area, the intermediate wall including an intermediate protrusion, wherein the mesh and the plug are maintained separate from each other within the package, and wherein the base protrusion and the intermediate protrusion extend in a direction toward the top of the first area.

* * * * *